United States Patent
Zheng et al.

(10) Patent No.: US 12,203,917 B2
(45) Date of Patent: Jan. 21, 2025

(54) METHOD FOR DETERMINING ORE-FORMING ENVIRONMENT OF PORPHYRY DEPOSIT BASED ON TOURMALINE COMPONENT

(71) Applicants: CHINA UNIVERSITY OF GEOSCIENCES (BEIJING), Beijing (CN); Tibet Julong Copper Co., Ltd., Lhasa (CN)

(72) Inventors: Youye Zheng, Beijing (CN); Jianzhou Yi, Beijing (CN); Peng Liu, Beijing (CN); Song Wu, Beijing (CN); Xiaofang Dou, Beijing (CN); Quansheng Shen, Lhasa (CN); Zhixin Zhang, Lhasa (CN); Jinling Liao, Lhasa (CN); Jiancuo Luosang, Lhasa (CN); Defu Shu, Lhasa (CN); Qiong Ci, Lhasa (CN); Xiaofeng Liu, Lhasa (CN)

(73) Assignees: CHINA UNIVERSITY OF GEOSCIENCES (BEIJING), Beijing (CN); Tibet Julong Copper Co., Ltd., Lhasa (CN)

( * ) Notice: Subject to any disclaimer, the term of this patent is extended or adjusted under 35 U.S.C. 154(b) by 0 days.

(21) Appl. No.: 18/597,929

(22) Filed: Mar. 7, 2024

(65) Prior Publication Data

US 2024/0426802 A1     Dec. 26, 2024

(30) Foreign Application Priority Data

Jun. 20, 2023   (CN) .................. 202310731550.X (51) Int. Cl.
*G01N 33/24*   (2006.01)
*G01N 1/28*    (2006.01)
*H01J 49/10*   (2006.01)

(52) U.S. Cl.
CPC ............ *G01N 33/24* (2013.01); *G01N 1/286* (2013.01); *H01J 49/105* (2013.01); *G01N 2001/2866* (2013.01)

(58) Field of Classification Search
CPC ................. G01N 33/24; G01N 1/286; G01N 2001/2866; H01J 49/105
(Continued)

(56) References Cited

U.S. PATENT DOCUMENTS

| 9,945,832 B2 | 4/2018 | Trobat et al. |
| 10,935,537 B2 | 3/2021 | Sointula et al. |
| 11,921,016 B1 | 3/2024 | Royer |

FOREIGN PATENT DOCUMENTS

| CN | 114076776 A | 2/2022 |
| CN | 115078520 A | 9/2022 |

(Continued)

OTHER PUBLICATIONS

Wu et al., CN115078520A, "Method for evaluating ore-bearing property of porphyry system based on mineral geochemistry", published: Sep. 20, 2022 (Year: 2022).*

(Continued)

*Primary Examiner* — John H Le
(74) *Attorney, Agent, or Firm* — True Shepherd LLC; Andrew C. Cheng (57) ABSTRACT

The present disclosure provides a method for determining an ore-forming environment of a porphyry deposit based on a tourmaline component, including the following steps: collecting a tourmaline-containing rock in the porphyry deposit to obtain a rock sample; performing pretreatment on the rock sample to obtain a treated sample; performing an in-situ tourmaline trace element test on the treated sample to obtain a test result; performing data processing and interpretation on the test result to obtain tourmaline trace element data;

(Continued)

establishing a discrimination factor based on the tourmaline trace element data; and determining the ore-forming environment based on the discrimination factor. The present disclosure can quickly recognize a forming environment of a newly discovered porphyry deposit, thereby summarizing a rule and quickly giving guidance for a next prospecting direction.

6 Claims, 3 Drawing Sheets

(58) Field of Classification Search
USPC .......................................................... 702/11
See application file for complete search history.

(56) References Cited

FOREIGN PATENT DOCUMENTS

| | | |
|---|---|---|
| CN | 115128247 A | 9/2022 |
| CN | 115684550 A | 2/2023 |

OTHER PUBLICATIONS

Qui et al. "Tourmaline composition and boron isotope signature as a tracer of magmatic-hydrothermal processes", published: Jul. 2021 (Year: 2021).*

* cited by examiner

METHOD FOR DETERMINING ORE-FORMING ENVIRONMENT OF PORPHYRY DEPOSIT BASED ON TOURMALINE COMPONENT

CROSS-REFERENCE TO RELATED APPLICATIONS

This application claims priority to Chinese Patent Application No. 202310731550.X with a filing date of Jun. 20, 2023. The content of the aforementioned application, including any intervening amendments thereto, is incorporated herein by reference.

TECHNICAL FIELD

The present disclosure relates to the field of exploration and evaluation, and in particular to a method and system for determining an ore-forming environment of a porphyry deposit based on a tourmaline component.

BACKGROUND

Porphyry deposits can be formed in different environments, such as subduction environment and collision environment. The porphyry deposits formed in different environments experience different ore-forming processes. For example, for the subduction of environment, the ore-forming magma was derived from the partial melting of the mantle wedge, while ore-forming magma from the collision environment was derived from the partial melting of the subduction-modified lower crust. Differences of the ore-forming processes may be manifested by constantly separating and crystallizing minerals in magma evolution or fluid exsolution. Tourmaline is common in the porphyry deposits. A crystalline structure of the tourmaline can contain various positive ions with different sizes and valence states, thus generating a complex type and component. Regardless of intracrystalline diffusion, the tourmaline can retain chemical impressions of melt or fluid from which it formed. Therefore, the tourmaline component can be used to effectively determine the forming environment of the porphyry deposit.

SUMMARY OF PRESENT INVENTION

An objective of the present disclosure is to provide a quantitative indicator of a tourmaline component for determining an ore-forming environment of a porphyry deposit, thereby quickly recognizing a forming environment of the porphyry deposit, and giving further guidance for mineral prospecting and exploration.

To achieve the above objective, the present disclosure provides a method for determining an ore-forming environment of a porphyry deposit based on a tourmaline component, including the following steps:
collecting a tourmaline-containing rock in the porphyry deposit to obtain a rock sample;
performing pretreatment on the rock sample to obtain a treated sample;
performing an in-situ tourmaline trace element test on the treated sample to obtain a test result;
performing data processing and interpretation on the test result to obtain tourmaline trace element data;
establishing a discrimination factor based on the tourmaline trace element data; and
determining the ore-forming environment based on the discrimination factor.

Preferably, the rock sample is obtained as follows: collecting the tourmaline-containing rock in the porphyry deposit, and recording collected information of the rock, where the collected information includes: a sample number, a sample position, lithology, alteration, mineralization, and an occurrence of tourmaline. Preferably, the pretreatment includes:
grinding a tourmaline-containing region in the rock sample into a thin section;
observing the thin section under a microscope and recognizing tourmaline; and
labeling the tourmaline to obtain the treated sample.

Preferably, the test result is obtained as follows: performing in-situ laser ablation inductively coupled plasma mass spectrometry (LA-ICP-MS) trace element analysis on the treated sample, tested elements including Li, Be, Sc, Ti, V, Cr, Mn, Co, Ni, Cu, Zn, Ga, Rb, Sr, Y, Zr, Nb, Sn, Sb, Ba, La, Ce, Pr, Nd, Sm, Eu, Gd, Tb, Dy, Ho, Er, Tm, Yb, Lu, Hf, Ta, Pb, Th, U, and REE (Rare Earth Element).

Preferably, the tourmaline trace element data is obtained as follows: importing the test result to ICPMSDataCal software; obtaining an integral curve of a trace element at each test point, and adjusting start time and end time of an integral curve at each observation point one by one according to a preset rule; removing invalid data according to an abnormal peak on the integral curve of the element; exporting a screened integral curve as an Excel file; removing non-tourmaline data by setting B=10,000-40,000 ppm in the Excel file, where B is a boron element; and obtaining the tourmaline trace element data.

Preferably, the discrimination factor is established as follows:
obtaining the tourmaline trace element data of the porphyry deposits in a subduction environment and a collision environment based on historical data; and
comparing a difference between the porphyry deposits in the subduction and the collision environment to establish the discrimination factor.

The present disclosure further provides a system for determining an ore-forming environment of a porphyry deposit based on a tourmaline component, including: a collection module, a pretreatment module, a detection module, an interpretation module, an establishment module, and a determination module.

The collection module is configured to collect a tourmaline-containing rock in a porphyry deposit to obtain a rock sample.

The pretreatment module is configured to perform pretreatment on the rock sample to obtain a treated sample.

The detection module is configured to perform an in-situ tourmaline trace element test on the treated sample to obtain a test result.

The interpretation module is configured to perform data processing and interpretation on the test result to obtain tourmaline trace element data.

The establishment module is configured to establish a discrimination factor based on the tourmaline trace element data.

The determination module is configured to determine an ore-forming environment based on the discrimination factor.

Preferably, the pretreatment module has a following workflow:
grinding a tourmaline-containing region in the rock sample into a thin section;
observing the thin section under a microscope and recognizing tourmaline; and
labeling the tourmaline to obtain the treated sample.

The present disclosure has the following beneficial effects over the prior art:

The present disclosure can quickly recognize a forming environment of a newly discovered porphyry deposit, thereby summarizing a rule and quickly giving guidance for a next prospecting direction.

BRIEF DESCRIPTION OF THE DRAWINGS

To describe the technical solutions in the embodiments of the present disclosure more clearly, the drawings required for describing the embodiments are briefly described below. Apparently, the drawings in the following description show merely some embodiments of the present disclosure, and those of ordinary skill in the art may still derive other drawings from these drawings without creative efforts.

DETAILED DESCRIPTION OF THE EMBODIMENTS

The technical solutions in the embodiments of the present disclosure are clearly and completely described below with reference to the drawings in the embodiments of the present disclosure. Apparently, the described embodiments are only some rather than all of the embodiments of the present disclosure. All other embodiments obtained by one of ordinary skill in the art based on the embodiments of the present disclosure without creative efforts shall fall within the protection scope of the present disclosure.

To make the above objectives, features, and advantages of the present disclosure more obvious and easier to understand, the present disclosure will be further described in detail with reference to the accompanying drawings and specific implementations.

In the disclosure, the term "thin section" has its common meaning in optical mineralogy and petrography. A thin section (or petrographic thin section) is a thin slice of a rock or mineral sample, prepared in a laboratory. A thin sliver of rock is cut from the sample with a diamond saw and ground optically flat. It is then mounted on a glass slide and then ground smooth using progressively finer abrasive grit until the sample is about 30 μm thick.

Embodiment 1

Figure 1:
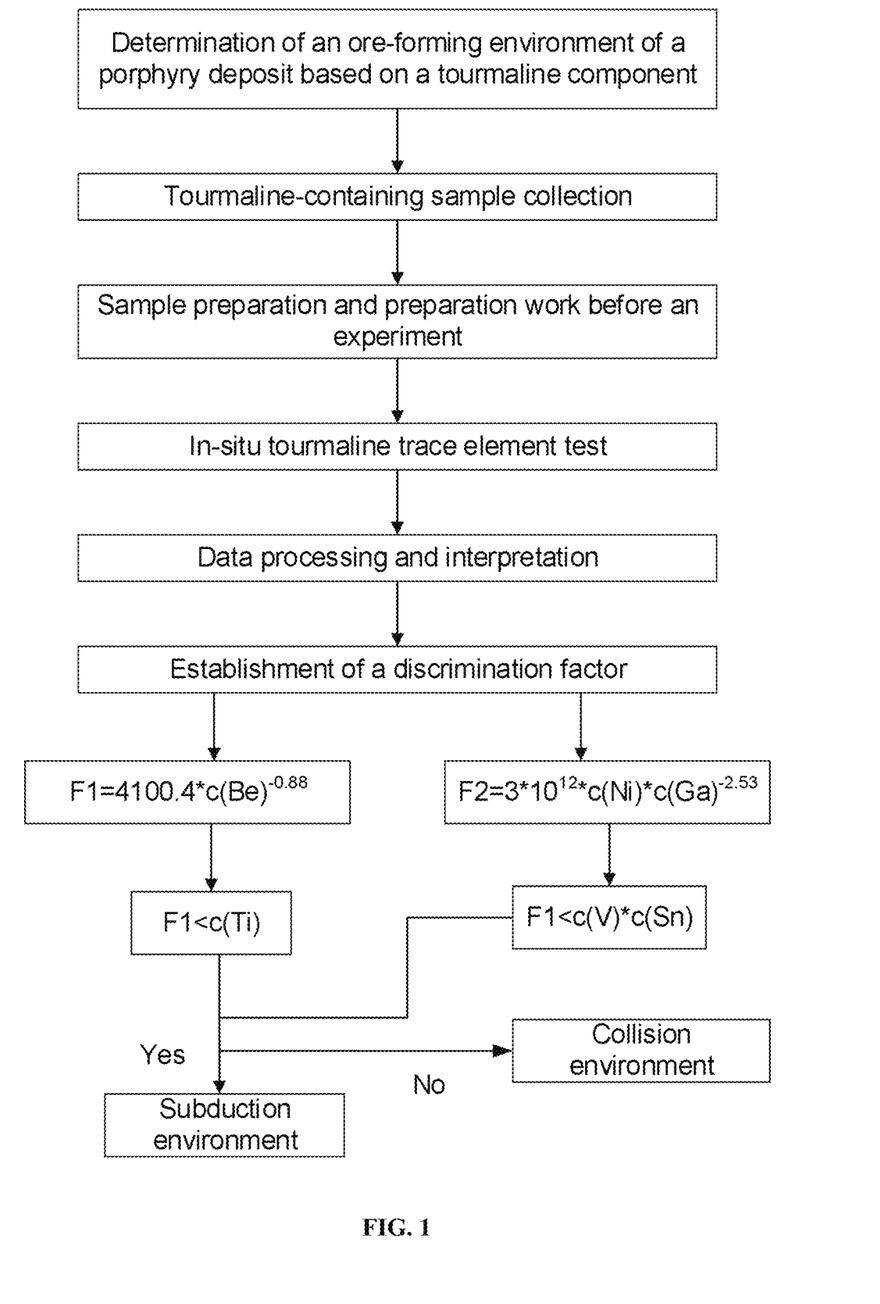
FIG. 1 is a schematic view illustrating a flowchart of a method according to an embodiment of the present disclosure.

FIG. 1 is a schematic view illustrating a flowchart of a method according to the embodiment.

A tourmaline-containing rock is collected in a porphyry deposit to obtain a rock sample. The tourmaline-containing rock is collected in the porphyry deposit, and collected information is obtained. The collected information includes a sample number, a sample position, lithology, alteration, mineralization and an occurrence of tourmaline.

Pretreatment is performed on the rock sample to obtain a treated sample. A tourmaline-containing region in the rock sample is ground into a thin section. The thin section is observed under a microscope and tourmaline is recognized. About 20 tourmaline particles with a size >30 μm are selected, and labeled with a marking pen.

An in-situ tourmaline trace element test is performed on the treated sample to obtain a test result, specifically including:

In-situ LA-ICP-MS trace element analysis is performed on the treated sample. In the embodiment, two standard samples (NIST SRM 610 and NIST SRM 612) are inserted every eight sample points, and one monitoring sample (GHVO-2) is inserted every ten sample points. Tested elements include Li, Be, Sc, Ti, V, Cr, Mn, Co, Ni, Cu, Zn, Ga, Rb, Sr, Y, Zr, Nb, Sn, Sb, Ba, La, Ce, Pr, Nd, Sm, Eu, Gd, Tb, Dy, Ho, Er, Tm, Yb, Lu, Hf, Ta, Pb, Th, U, and REE.

Data processing and interpretation are performed on the test result to obtain tourmaline trace element data. The test result is imported to ICPMSDataCal software. An integral curve of a trace element at each test point is obtained, and start time and end time of an integral curve at each observation point are adjusted one by one according to a preset rule. The preset rule is provided to ensure that the selected integral curve of the element has a flattest and widest signal range. Invalid data is removed according to an abnormal peak on the integral curve of the element. A screened integral curve is exported as an Excel file. Non-tourmaline data is removed by setting B=10,000-40,000 ppm in the Excel file, B being a boron element, thereby obtaining the tourmaline trace element data. Data is tourmaline data if a content of the boron element falls within a range of 10,000-40,000 ppm. Or otherwise, the data is the non-tourmaline data, and is removed.

A discrimination factor is established based on the tourmaline trace element data. The tourmaline trace element data of the porphyry deposit in a subduction environment and a collision environment are obtained based on historical data. The historical data comes from issued periodicals or theses on the porphyry deposits. For different elements, boxplots are drawn to compare which elements are different in the two environments (the porphyry deposit in the subduction environment and the porphyry deposit in the collision environment). Compared with the porphyry deposit in the subduction environment, the porphyry deposit in the collision environment shows an obviously high content of Be and Ti, and a slightly high content of Ga, Ni, Sn, and V. Therefore, the content of Be, Ti, Ni, Ga, V, and Sn is defined as c(Be), c(Ti), c(Ni), c(Ga), c(V) and c(Sn).

(1) The discrimination factor F1 is calculated.

A binary diagram is used directly to determine obviously different element contents in the two environments. A graph (FIG. 2a) is plotted with Be as an abscissa and Ti as an ordinate. A boundary between the subduction environment and the collision environment is obtained according to a range on the plotted graph. The discrimination factor is calculated by:

$$F1: F1 = 4100.4 * c(Be)^{-0.88} \quad (1)$$

(2) The discrimination factor F2 is calculated.

For slightly different element contents in the two environments, the elements are multiplied pairwise to amplify differences of the element contents in different environments. Then, a binary diagram is used for determination. A graph (FIG. 2b) is plotted with Ni*Ga as an abscissa and V*Sn as an ordinate. A boundary between the subduction environment and the collision environment is obtained according to a range on the plotted graph. The discrimination factor is calculated by:

$$F2: F2 = 3 * 10^{12} * (c(Ni) * c(Ga))^{-2.53} \quad (2)$$

Figure 2:
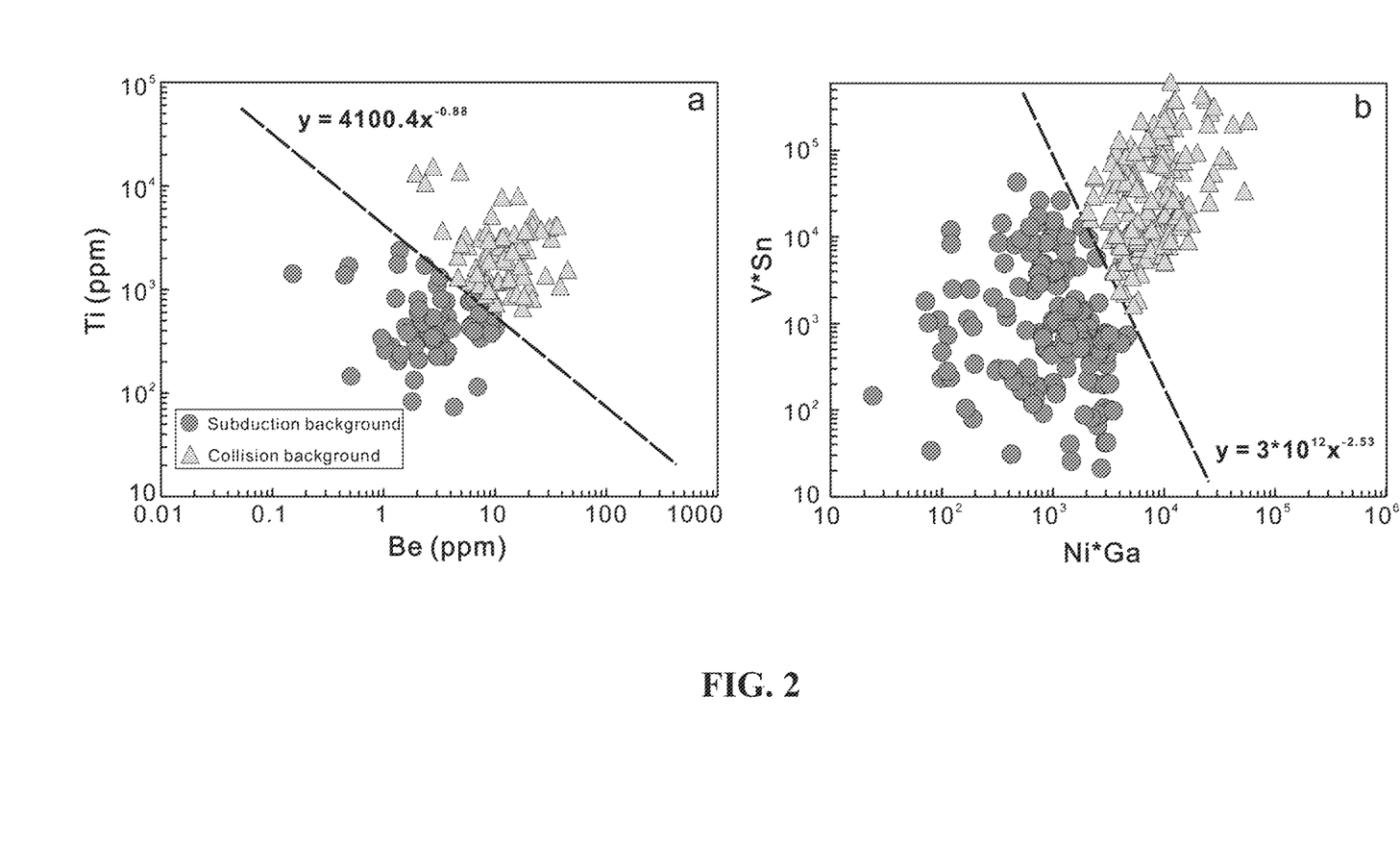
FIG. 2 is a schematic view illustrating a determination result according to an embodiment of the present disclosure, (a) being a graph plotted with Be as an abscissa and Ti as an ordinate, and (b) being a graph plotted with Ni*Ga as an abscissa and V*Sn as an ordinate.

The ore-forming environment is determined based on the discrimination factor. According to the tourmaline trace element data obtained in the above step, the obtained Be content is brought into Eq. (1) to calculate the discrimination factor F1. If c(Ti)>F1, the subduction environment is determined. Or otherwise, the collision environment is determined. The Ni content and the Ga content are brought into Eq. (2) to calculate the discrimination factor F2. If c(V)*c(Sn)>F2, the subduction environment is determined. Or otherwise, the collision environment is determined. A final result is shown in FIG. 2.

Embodiment 2

A feasibility of the present disclosure is verified below in combination with the embodiment. The ore-forming environment of the porphyry deposit is determined with the tourmaline component. The Beimulang porphyry Cu deposit in Tibet is used as an example:

a. A sample is collected. A tourmaline-containing sample is collected in the Beimulang deposit, and information is recorded (as shown in Table 1).

TABLE 1

| Sample No. | X | Y | Lithology | Alteration | Mineralization | Tourmaline characteristic |
|---|---|---|---|---|---|---|
| ZK0201 | 544819 | 3280700 | Monzogranite porphyry | Potassic alteration | None | Disseminated |
| ZK0001 | 544974 | 3281101 | Monzogranite | Potassic alteration | None | Veined |
| ZK0501 | 544216 | 3285961 | Monzogranite | Phyllic alteration | Little chalcopyrite mineralization | Nodule |
| ... | ... | ... | ... | ... | ... | ... | b. The sample is prepared. A tourmaline-containing region is selected and prepared as a thin section. Tourmaline in the thin section is recognized under a microscope, and about 20 tourmaline particles with a size >30 μm are labeled.

c. The sample is tested. An in-situ LA-ICP-MS trace element analyzer is used to test the sample.

d. Data is processed and interpreted. Test data obtained is processed with ICPMSDataCal software, including (1) data importing, (2) data interpretation, and (3) data screening.

e. An ore-forming environment is determined. According to final data (Table 2) processed with Excel, as well as the calculated discrimination factor F1 and the calculated discrimination factor F2, it is determined that the tourmaline component collected in the Beimulang deposit is formed in the collision environment. This coincides with the geological fact.

TABLE 2

| Environment | Sample No. | Type | Be | Ti | V | Ni | Ga | Sn |
|---|---|---|---|---|---|---|---|---|
| Collision | 2-395-1-2 | Tourmaline nodule | 8.23 | 1336.56 | 710.22 | 44.77 | 75.50 | 61.92 |
| Collision | 2-395-1-8 | Tourmaline nodule | 7.63 | 1951.12 | 659.43 | 171.66 | 91.34 | 197.69 |
| Collision | 2-395-1-3 | Tourmaline nodule | 27.47 | 1343.37 | 917.32 | 64.69 | 82.65 | 86.18 |
| Collision | 2-395-1-10 | Tourmaline nodule | 10.29 | 2156.14 | 835.77 | 114.72 | 56.47 | 53.08 |
| Collision | 2-395-1-1 | Tourmaline nodule | 5.54 | 2573.98 | 955.18 | 184.24 | 55.47 | 97.48 |
| Collision | 2-395-1-12 | Tourmaline nodule | 7.31 | 1146.11 | 799.67 | 50.71 | 99.61 | 67.12 |
| Collision | 2-395-1-6 | Tourmaline nodule | 19.56 | 1031.88 | 1961.47 | 247.53 | 88.49 | 340.39 |
| Collision | 2-395-1-11 | Tourmaline nodule | 17.33 | 1665.74 | 1049.19 | 68.37 | 75.91 | 69.99 |
| Collision | 2-395-1-7 | Tourmaline nodule | 8.07 | 1212.15 | 800.15 | 87.97 | 52.20 | 109.63 |
| Collision | 2-395-1-4 | Tourmaline nodule | 10.37 | 1178.98 | 623.71 | 30.43 | 70.32 | 35.58 |
| Collision | 2-395-1-5 | Tourmaline nodule | 13.40 | 1414.70 | 784.51 | 69.58 | 64.49 | 17.05 |
| Collision | 2-395-1-9 | Tourmaline nodule | 8.41 | 2215.10 | 757.27 | 93.63 | 104.37 | 168.53 |

TABLE 2-continued

| Environment | Sample No. | Type | Be | Ti | V | Ni | Ga | Sn |
|---|---|---|---|---|---|---|---|---|
| Collision | 3-240-1-1 | Tourmaline vein | 5.80 | 1169.91 | 631.15 | 92.32 | 87.87 | 487.21 |
| Collision | 3-240-1-2 | Tourmaline vein | | 313.81 | 367.60 | 30.92 | 103.47 | 60.77 |
| Collision | 3-240-1-3 | Tourmaline vein | 9.47 | 2191.19 | 759.54 | 104.94 | 101.47 | 602.64 |
| Collision | 3-240-1-4 | Tourmaline vein | 3.53 | 765.79 | 429.32 | 35.19 | 134.34 | 173.85 |
| Collision | 3-240-1-5 | Tourmaline vein | 12.74 | 1828.00 | 731.39 | 105.34 | 104.44 | 375.57 |
| Collision | 3-240-1-6 | Tourmaline vein | 8.04 | 1121.91 | 951.50 | 67.30 | 166.07 | 405.53 |
| Collision | 3-240-1-7 | Tourmaline vein | 18.96 | 2352.43 | 574.90 | 128.07 | 116.19 | 576.81 |
| Collision | 3-240-Z-1 | Tourmaline vein | 12.10 | 2419.53 | 858.08 | 118.66 | 97.27 | 1116.28 |
| Collision | 3-240-Z-2 | Tourmaline vein | 3.74 | 738.49 | 674.15 | 84.56 | 106.55 | 379.86 |
| Collision | 3-240-Z-3 | Tourmaline vein | | 556.85 | 558.03 | 57.11 | 116.75 | 276.82 |
| Collision | 3-240-Z-4 | Tourmaline vein | 12.96 | 1219.67 | 346.20 | 47.82 | 95.36 | 360.58 |
| Collision | 3-240-Z-5 | Tourmaline vein | 9.29 | 881.56 | 545.64 | 51.75 | 105.69 | 258.02 |
| Collision | 3-240-Z-6 | Tourmaline vein | 10.71 | 2541.54 | 825.60 | 130.23 | 97.23 | 710.30 |
| Collision | 3-240-Z-7 | Tourmaline vein | 3.28 | 3627.51 | 1357.26 | 106.21 | 95.55 | 258.49 |
| Collision | 3-240-Z-8 | Tourmaline vein | 4.74 | 13266.72 | 506.76 | 114.35 | 67.20 | 72.66 |
| Collision | 5-003-1 | Tourmaline vein | 1.90 | 12922.95 | 529.96 | 74.44 | 57.81 | 63.86 |
| Collision | 5-003-2 | Tourmaline vein | | 14250.82 | 490.94 | 129.52 | 73.14 | 200.64 |
| Collision | 5-003-3 | Tourmaline vein | 9.86 | 726.56 | 173.75 | 48.73 | 47.87 | 399.62 |
| Collision | 5-003-4 | Tourmaline vein | 6.57 | 1593.95 | 179.95 | 48.89 | 48.46 | 406.50 |
| Collision | 5-003-5 | Tourmaline vein | 2.69 | 14988.70 | 549.03 | 62.24 | 61.85 | 149.70 |
| Collision | 5-003-6 | Tourmaline vein | 7.13 | 3064.27 | 234.52 | 50.27 | 45.63 | 176.29 |
| Collision | 5-003-7 | Tourmaline vein | 7.96 | 875.13 | 457.94 | 109.40 | 89.08 | 18.21 |
| Collision | 4-001-1-1 | Disseminated tourmaline | 37.16 | 1055.27 | 241.55 | 65.32 | 88.94 | 10.05 |
| Collision | 4-001-1-2 | Disseminated tourmaline | 6.99 | 1089.47 | 190.72 | 47.69 | 65.16 | 9.98 |
| Collision | 4-001-1-3 | Disseminated tourmaline | 8.52 | 968.78 | 283.95 | 85.55 | 71.94 | 17.19 |
| Collision | 4-001-1-4 | Disseminated tourmaline | 5.96 | 468.59 | 90.12 | 26.09 | 50.05 | 4.58 |
| Collision | 4-001-1-5 | Disseminated tourmaline | 17.36 | 1325.32 | 191.42 | 97.47 | 54.48 | 11.03 |
| Collision | 6-228-2 | Tourmaline vein | 14.49 | 3364.26 | 240.55 | 297.95 | 37.19 | 61.56 |
| Collision | 6-228-3 | Tourmaline vein | 13.00 | 1242.27 | 584.35 | 103.59 | 49.60 | 111.02 |
| Collision | 6-228-4 | Tourmaline vein | 43.19 | 1529.49 | 1242.92 | 69.25 | 57.06 | 156.24 |
| Collision | 6-228-5 | Tourmaline vein | 18.10 | 3608.92 | 1371.91 | 88.28 | 80.42 | 144.48 |
| Collision | 6-228-6 | Tourmaline vein | 8.21 | 3526.91 | 1312.34 | 81.69 | 75.95 | 248.60 |

Embodiment 3

Figure 3:
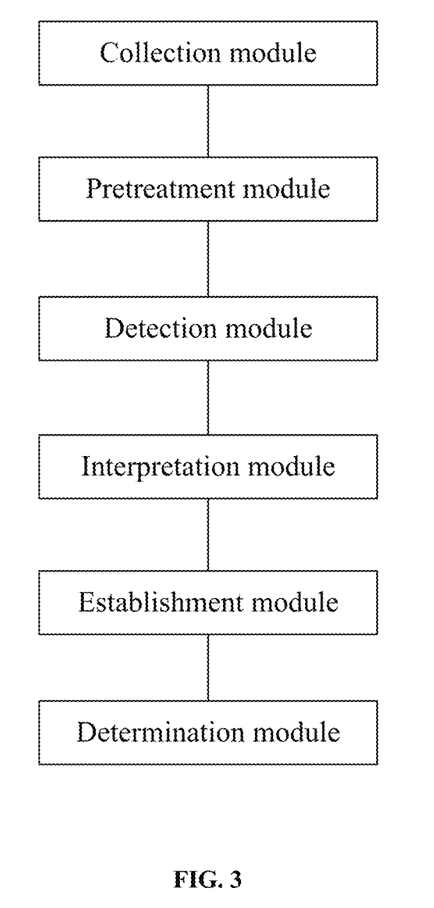
FIG. 3 is a schematic structural view of a system according to an embodiment of the present disclosure.

FIG. 3 is a schematic structural view of a system according to the embodiment. The system includes a collection module, a pretreatment module, a detection module, an interpretation module, an establishment module, and a determination module. The collection module is configured to collect a tourmaline-containing rock in a porphyry deposit to obtain a rock sample. The pretreatment module is configured to perform pretreatment on the rock sample to obtain a treated sample. The detection module is configured to perform an in-situ tourmaline trace element test on the treated sample to obtain a test result. The interpretation module is configured to perform data processing and interpretation on the test result to obtain tourmaline trace element data. The establishment module is configured to establish a discrimination factor based on the tourmaline trace element data. The determination module is configured to determine an ore-forming environment based on the discrimination factor.

With reference to the embodiment, detailed descriptions on how to solve a technical problem in real life will be provided below.

The collection module collects a tourmaline-containing rock in a porphyry deposit to obtain a rock sample. The tourmaline-containing rock is collected in the porphyry deposit, and collected information is obtained. The collected information includes a sample number, a sample position, lithology, alteration, mineralization, and an occurrence of tourmaline.

The pretreatment module performs pretreatment on the rock sample to obtain a treated sample. A tourmaline-containing region in the rock sample is ground into a thin section. The thin section is observed under a microscope and tourmaline is recognized. About 20 tourmaline particles with a size >30 μm are selected, and labeled with a marking pen.

The detection module performs an in-situ tourmaline trace element test on the treated sample to obtain a test result, specifically including:

In-situ LA-ICP-MS trace element analysis is performed on the treated sample. In the embodiment, two standard samples (NIST SRM 610 and NIST SRM 612) are inserted every eight sample points, and one monitoring sample (GHVO-2) is inserted every ten sample points. Tested elements include Li, Be, Sc, Ti, V, Cr, Mn, Co, Ni, Cu, Zn, Ga, Rb, Sr, Y, Zr, Nb, Sn, Sb, Ba, La, Ce, Pr, Nd, Sm, Eu, Gd, Tb, Dy, Ho, Er, Tm, Yb, Lu, Hf, Ta, Pb, Th, U, and REE.

The interpretation module performs data processing and interpretation on the test result to obtain tourmaline trace element data. The test result is imported to ICPMSDataCal software. An integral curve of a trace element at each test point is obtained, and start time and end time of an integral curve at each observation point are adjusted one by one according to a preset rule. The preset rule is provided to ensure that the selected integral curve of the element has a flattest and widest signal range. Invalid data is removed according to an abnormal peak on the integral curve of the element. A screened integral curve is exported as an Excel file. Non-tourmaline data is removed by setting B=10,000-40,000 ppm in the Excel file, B being a boron element, thereby obtaining the tourmaline trace element data. For the data in the Excel file, it is the tourmaline data if a content of the boron element falls within a range of 10,000-40,000 ppm. Or otherwise, the data is the non-tourmaline data, and is removed.

The establishment module establishes a discrimination factor based on the tourmaline trace element data. The tourmaline trace element data of the porphyry deposit in a subduction environment and the tourmaline trace element data of the porphyry deposit in a collision environment are obtained based on historical data. The historical data comes from issued periodicals or theses on the porphyry deposits. For each element, boxplots are drawn to compare the differences in the two environments (the porphyry deposit in the subduction environment and the porphyry deposit in the collision environment). Compared with the porphyry deposit in the subduction environment, the porphyry deposit in the collision environment shows an obviously high content of Be and Ti, and a slightly high content of Ga, Ni, Sn, and V. Therefore, the content of Be, Ti, Ni, Ga, V, and Sn is defined as $c(Be)$, $c(Ti)$, $c(Ni)$, $c(Ga)$, $c(V)$ and $c(Sn)$.

(1) The discrimination factor F1 is calculated.

A binary diagram is used directly to determine obviously different element contents in the two environments. A graph is plotted with Be as an abscissa and Ti as an ordinate. A boundary between the subduction environment and the collision environment is obtained according to a range on the plotted graph. The discrimination factor is calculated by:

$$F1:F1=4100.4*c(Be)^{-0.88} \quad (3)$$

(2) The discrimination factor F2 is calculated.

For slightly different element contents in the two environments, the elements are multiplied pairwise to amplify differences of the element contents in different environments. Then, a binary diagram is used for determination. A graph is plotted with Ni*Ga as an abscissa and V*Sn as an ordinate. A boundary between the subduction environment and the collision environment is obtained according to a range on the plotted graph. The discrimination factor is calculated by:

$$F2:F2=3*10^{12}*(c(Ni)*c(Ga))^{-2.53} \quad (4)$$

The determination module determines an ore-forming environment based on the discrimination factor. According to the tourmaline trace element data obtained in the above process, the obtained Be content is brought into Eq. (3) to calculate the discrimination factor F1. If $c(Ti)>F1$, the subduction environment is determined. Or otherwise, the collision environment is determined. The Ni content and the Ga content are brought into Eq. (4) to calculate the discrimination factor F2. If $c(V)*c(Sn)>F2$, the subduction environment is determined. Or otherwise, the collision environment is determined.

The above embodiments are only intended to describe the preferred implementations of the present disclosure, but not to limit the scope of the present disclosure. Various alterations and improvements made by those of ordinary skill in the art based on the technical solution of the present disclosure without departing from the design spirit of the present disclosure shall fall within the scope of the appended claims of the present disclosure.

What is claimed is:

1. A method for determining an ore-forming environment of a porphyry deposit based on a tourmaline component, comprising the following steps:

collecting a tourmaline-containing rock in the porphyry deposit to obtain a rock sample;

performing pretreatment on the rock sample to obtain a treated sample;

performing an in-situ tourmaline trace element test on the treated sample to obtain a test result;

performing data processing and interpretation on the test result to obtain tourmaline trace element data;

establishing a discrimination factor based on the tourmaline trace element data;

comprising the following steps:

the discrimination factor F1 is calculated;

a binary diagram is used directly to determine obviously different element contents in the two environments; a graph is plotted with Be as an abscissa and Ti as an ordinate; a boundary between the subduction environment and the collision environment is obtained according to a range on the plotted graph; the discrimination factor is calculated by:

$$F1:F1=4100.4*c(Be)^{-0.88} \quad (1)$$

the discrimination factor F2 is calculated;

for slightly different element contents in the two environments, the elements are multiplied pairwise to amplify differences of the element contents in different environments; then, a binary diagram is used for determination; a graph is plotted with Ni*Ga as an abscissa and V*Sn as an ordinate; a boundary between the subduction environment and the collision environment is obtained according to a range on the plotted graph; the discrimination factor is calculated by:

$$F2: F2 = 3*10^{12}*(c(Ni)*c(Ga))^{-2.53} \quad (2)$$

determining the ore-forming environment based on the discrimination factor; comprising the following steps: the obtained Be content is brought into Eq. (1) to calculate the discrimination factor F1; if c(Ti)>F1, the subduction environment is determined; or otherwise, the collision environment is determined; the Ni content and the Ga content are brought into Eq. (2) to calculate the discrimination factor F2; if c(V)*c(Sn)>F2, the subduction environment is determined; or otherwise, the collision environment is determined.

2. The method according to claim 1, wherein the rock sample is obtained as follows: collecting the tourmaline-containing rock in the porphyry deposit, and recording collected information of the rock, wherein the collected information comprises: a sample number, a sample position, lithology, alteration, mineralization and an occurrence of tourmaline.

3. The method according to claim 1, wherein the pretreatment comprises:
grinding a tourmaline-containing region in the rock sample into a thin section;
observing the thin section under a microscope and recognizing tourmaline; and
labeling the tourmaline to obtain the treated sample.

4. The method according to claim 1, wherein the test result is obtained as follows: performing in-situ laser ablation inductively coupled plasma mass spectrometry (LA-ICP-MS) trace element analysis on the treated sample, wherein tested elements comprise Li, Be, Sc, Ti, V, Cr, Mn, Co, Ni, Cu, Zn, Ga, Rb, Sr, Y, Zr, Nb, Sn, Sb, Ba, La, Ce, Pr, Nd, Sm, Eu, Gd, Tb, Dy, Ho, Er, Tm, Yb, Lu, Hf, Ta, Pb, Th, U, REE.

5. The method according to claim 1, wherein the tourmaline trace element data is obtained as follows: importing the test result to ICPMSDataCal software; obtaining an integral curve of a trace element at each test point, and adjusting start time and end time of an integral curve at each observation point one by one according to a preset rule; removing invalid data according to an abnormal peak on the integral curve of the element; exporting a screened integral curve as an Excel file; removing non-tourmaline data by setting B=10,000–40,000 ppm in the Excel file, wherein B is a boron element; and obtaining the tourmaline trace element data.

6. The method according to claim 1, wherein the discrimination factor is established as follows:
obtaining the tourmaline trace element data of the porphyry deposit in a subduction environment and the tourmaline trace element data of the porphyry deposit in a collision environment based on historical data; and
comparing a difference between the porphyry deposit in the subduction environment and the porphyry deposit in the collision environment to establish the discrimination factor.

* * * * *